Figure 1:
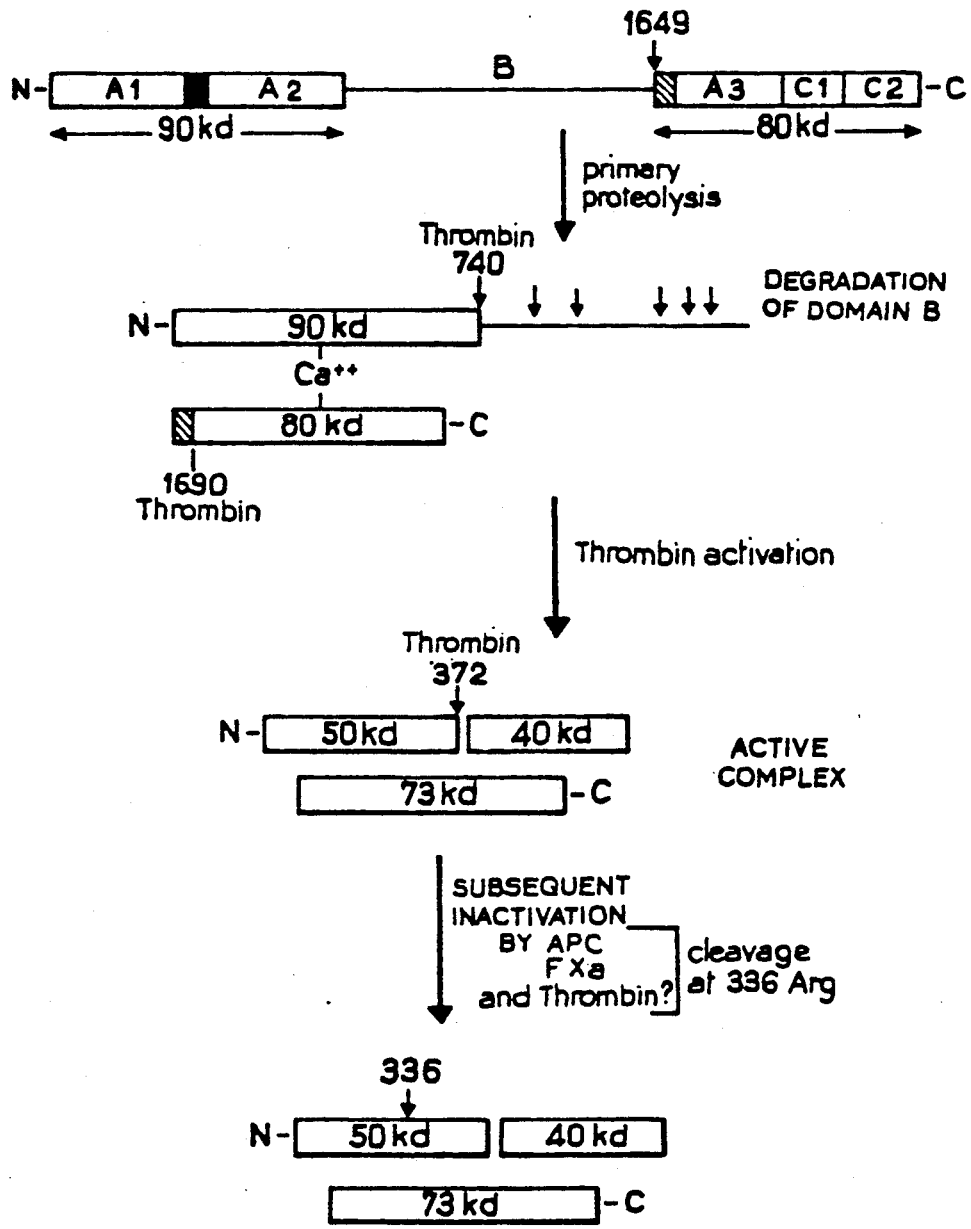

United States Patent [19]

Meulien et al.

[11] Patent Number: 5,112,950
[45] Date of Patent: May 12, 1992

[54] FACTOR VIII ANALOG, PREPARATION PROCESS, AND PHARMACEUTICAL COMPOSITION CONTAINING IT

[75] Inventors: Pierre Meulien; Andrea Pavirani, both of Strasbourg, France

[73] Assignee: Transgene S.A., Courbevoie, France

[21] Appl. No.: 723,666

[22] Filed: Jun. 26, 1991

Related U.S. Application Data

[63] Continuation of Ser. No. 228,265, Aug. 4, 1988, abandoned.

Foreign Application Priority Data

Aug. 11, 1987 [FR] France .................. 87 11415

[51] Int. Cl.⁵ .................. C07K 13/00; A61K 37/00
[52] U.S. Cl. .................. 530/383; 530/395; 514/8; 514/12; 435/69.6
[58] Field of Search .................. 530/381, 383; 514/7, 514/8, 12, 21; 435/69.6

[56] References Cited

FOREIGN PATENT DOCUMENTS

WO8606101 10/1986 PCT Int'l Appl. .................. 530/383

OTHER PUBLICATIONS

Brickhouse et al., "Purified Human Factor VIII Procoagulant Protein: Comparative Hemostatic Response After Infusions into Hemophilic and von Willebrand Disease Dogs", Proc. Natl. Acad. Sci., vol. 82 (Dec. 1985), 8752-8756.

Vehar et al., "Structure of Human Factor VIII", Nature, vol. 312 (Nov. 1984), p. 337.

Leyte et al., "The Interaction Between Human Blood-Coagulation Factor VIII and von Willebrand Factor", Biochem. J., 257 (1989), pp. 679-683.

Foster et al., "An immunogenic Region Within Residues $Val^{1670}$-$Glu^{1684}$ of the Factor VIII Light Chain Induces Antibodies Which Inhibit Binding of Factor VIII to von Willebrand Factor", J. of Biological Chemistry, vol. 263, No. 11 (Apr. 1988), pp. 5230-5234.

Foster et al., "A Synthetic Factor VIII Peptide of Eight Amino Acid Residues (1677-1684) Contains the Binding Region of an Anti-Factor VIII Antibody which Inhibits the Binding of Factor VIII to von Willebrand Factor," Thrombosis and Haemostasis—F. K. Schattauer Verlagsgesellschaft mbH. pp. 403-406.

French Search Resrport, Apr. 1988.

Toole et al.: "A Large Region (95 kDa) of Human Factor VIII is Dispensible for in Vitro Procoagulant Activity", Proc. Natl. Acad. Sci. USA, vol. 83, pp. 5939-5942, Aug. 1986, Biochemistry.

Eaton et al.: "Construction and Characterization of an Active Factor VIII Variant Lacking the Central One-Third of the Molecule", Biochemistry, vol. 25, No. 26, Dec. 30, 1986.

Primary Examiner—Robert A. Wax
Assistant Examiner—R. Keith Baker
Attorney, Agent, or Firm—Cushman, Darby & Cushman

[57] ABSTRACT

Factor VIII analog which has undergone deletion of amino acids 771 to 1666, prepared from eukaryotic cells transformed by an expression vector carrying the cDNA of the factor VIII which has undergone deletion.

6 Claims, 3 Drawing Sheets

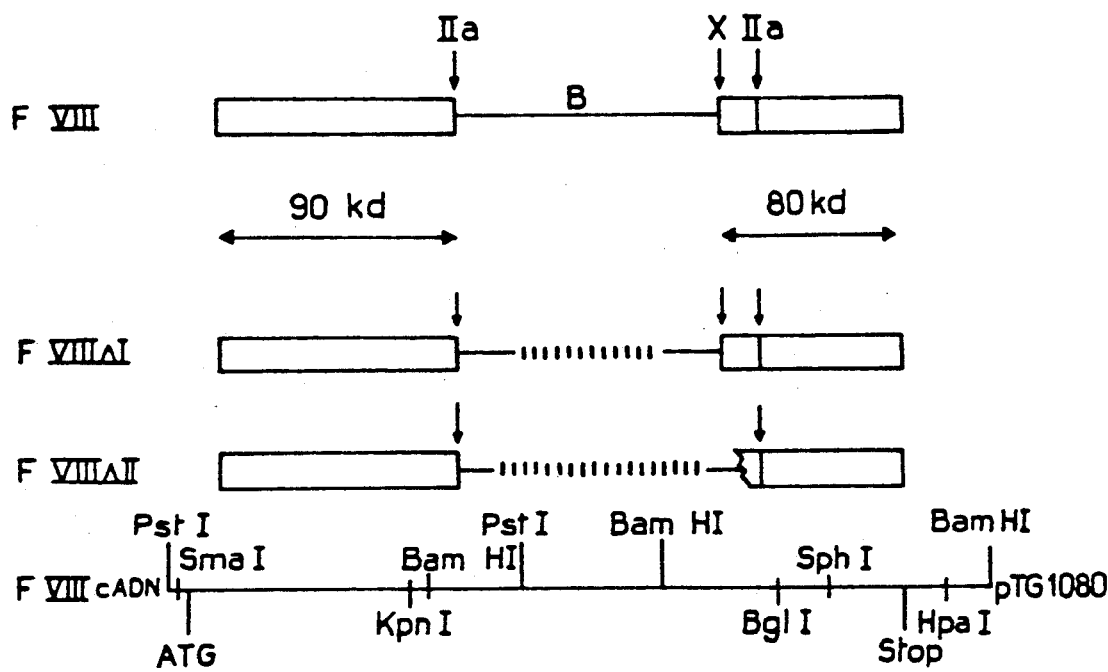
FIG_2
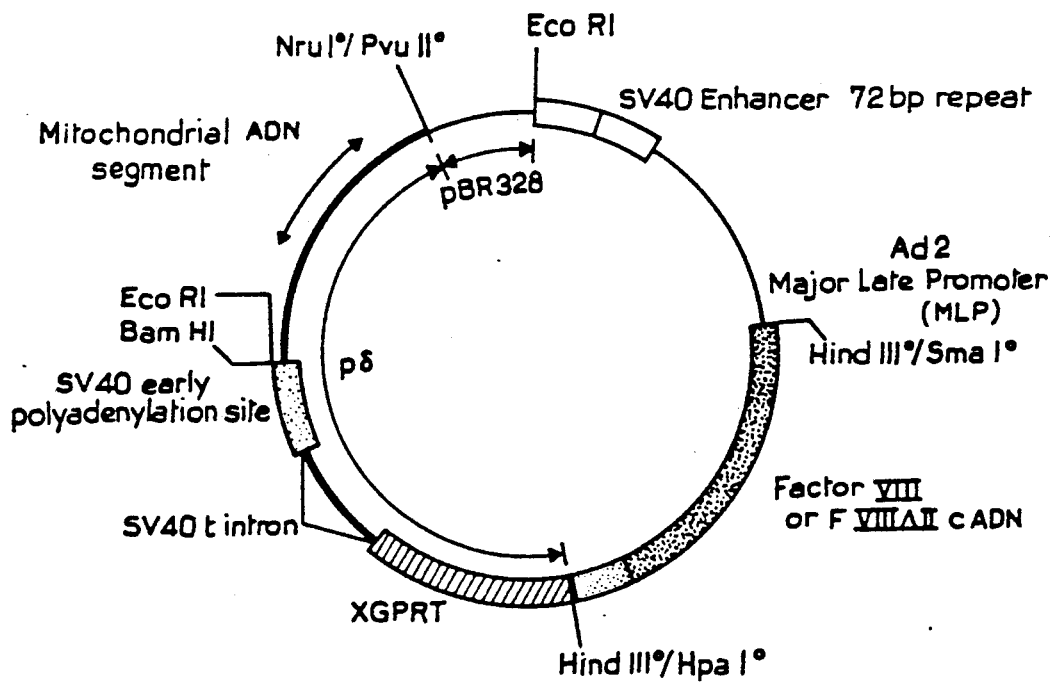
FIG_3

FACTOR VIII ANALOG, PREPARATION PROCESS, AND PHARMACEUTICAL COMPOSITION CONTAINING IT

This is a continuation of application Ser. No. 07/228,265, filed on Aug. 4, 1988, which was abandoned upon the filing hereof.

Cloning of the cDNA of factor VIII (FVIII) (1-3) has enabled a better understanding of the structure and functions of this complex molecule.

The first translation product of the mRNA is a molecule of 2,351 amino acids comprising a signal peptide of 19 amino acids. Internal homologies are observed in the amino acid sequences, which enable domains to be defined: a triplet of domains A, a single domain B and a pair of domains C, arranged in the following order: A1-A2-B-A3-C1-C2 (2, 4).

The single domain B is encoded by a 3,100-bp exon (exon 14 of the FVIII gene) (5), and contains 19 of the 25 potential glycosylation sites (Asn); this portion of the molecule is cleaved and lost during activation by thrombin (2, 4, 6).

The current model of the mechanism of maturation of factor VIII is shown schematically in FIG. 1.

In this model, the initial activation is due to a cleavage of the molecule between amino acids $Arg^{1648}$ and $Glu^{1649}$, which gives an 80-kd light-chain precursor and a >200 kd heavy-chain precursor.

The two chains are probably joined via a metal ion ($Ca^{--}$?) before the cleavage takes place.

Domain B is then degraded by several proteolytic cleavages, after which activation by thrombin is accomplished by a cleavage between amino acids $Arg^{739}$ and $Ser^{740}$ and between $Arg^{1689}$ and $Ser^{1690}$, which gives a 90-kd heavy chain and a 73-kd light chain. The need for a further cleavage between $Arg^{371}$ and $Ser^{372}$ to obtain maximal activation is still debatable; this cleavage might, on the contrary, destabilize the molecule (6, 7).

It is generally accepted that a prolonged incubation in the presence of thrombin leads to a rapid decrease in activity. Other factors can also inactivate factor VIII, such as activated protein C and factor Xa which cleaves the molecule at several points in particular at $Arg^{336}/Met^{337}$ (7).

In this maturation process, it is commented that domain B does not play a part in the activity of the mature molecule, since it is lost after activation by thrombin. In addition, Toole et al (8) have compared the nucleotide sequences of the genes for human and porcine factor VIII and have shown that the two B domains are highly divergent whereas the heavy and light chains are highly conserved.

This suggests (8, 9, 10, 11) that a molecule devoid of domain B would not lose its procoagulant function.

Two approaches have been followed in order to test this hypothesis: either the deletion, in the cDNA, of large DNA fragments corresponding to domain B, which gives shorter factor VIII derivatives (8, 9), or the coexpression in mammalian cells of DNA fragments corresponding to the heavy and light chains (10, 11).

The coexpression of heavy and light chains in mammalian cells results in a detectable production of FVIII:C, but at a level 5- times lower than that obtained by the expression of the complete module. This suggests that the combination of the two chains is inefficient, thereby decreasing the activity of the molecule (10, 11).

These experiments showed that a molecule devoid of most of domain B, but which has retained the maturation sites corresponding to amino acids 740, 1649 and 1690 (which appear to be necessary for the activation), exhibits normal procoagulant activity and, moreover, has the advantage of being expressed 10 times more efficiently in mammalian cells (8). This molecule can be activated by thrombin in the same manner as the complete natural molecule (9).

Factor VIII circulating in the plasma is combined with the von Willebrand factor (vWf), which appears to stabilize it; in effect, the half-life of FVIII in vivo decreases very strongly in the absence of vWf (16).

Eaton et al (9) have described a factor VIII derivative which has undergone deletion in domain B and which binds vWf efficiently, thereby enabling a normal half-life in vivo to be expected for the molecule which has undergone deletion of domain B.

The present invention relates to the factor VIII analog in which amino acids 771 to 1666 have been deleted. It will also be referred to throughout the description and the examples as FVIII66II.

The factor VIII analog according to the present invention is preferably prepared from a culture of eukaryotic cells that produce the said analog on a suitable culture medium, and the factor VIII obtained is separated.

The cells have preferably, according to the invention, been infected with a recombinant viral vector such as vaccinia virus, which provides the expression of the cDNA of the factor VIII analog in the cells. The latter are preferably BHK21 cells.

However, in the context of the present invention, it is also possible to transfect the cells with an integration vector containing the cDNA of the factor VIII analog, surrounded by the elements necessary for its expression in eukaryotic cells and a DNA segment that promotes the integration of the vector in the cellular DNA.

In this case, the cDNA coding for the factor VIII analog is preferably inserted in front of a gene coding for a selection marker, to give a bicistronic transcription product.

The transfected cells are preferably CHO cells.

Finally, the present invention relates to a pharmaceutical composition containing, by way of active principle, the factor VIII analog of the present invention.

Such a composition can contain, in addition, the von Willebrand factor.

The pharmaceutical composition of the present invention is preferably presented in sterile injectable form.

The present invention will be better understood on reading the examples, which are illustrated by means of the following figures:

FIG. 1: Diagram of the maturation of the factor VIII molecule by successive proteolytic cleavages (from Toole et al. 1984 (2) and Eaton et al. 1986 (7)).

FIG. 2: Diagram of the factor VIII molecule and of the 2 deletions ΔI (aa 868 to 1562) and ΔII (aa 771 to 1666).

The sites of cleavage by thrombin (IIa) and by an unknown protease ($X_1$ at position 1649) are indicted by arrows.

The bottom line represents the sequence of the cDNA, with the restriction sites used in the various constructions.

FIG. 3: Diagram of the rFVIII expression vector used for transforming CHO cells.

Figure 4:
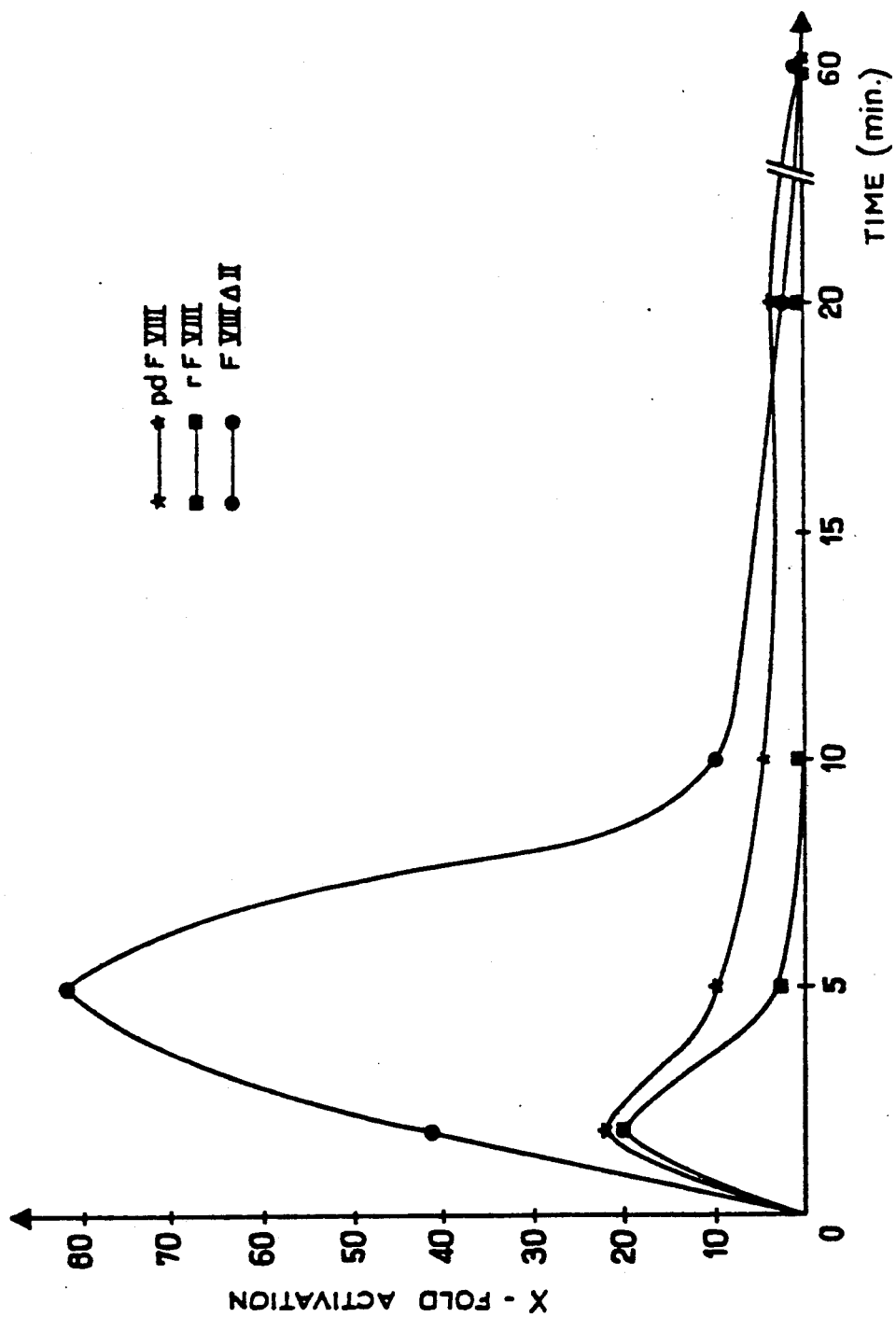

FIG. 4: Kinetics of activation by thrombin of the different factor VIII molecules:
pd = plasma derivative
r = intact recombinant molecule
ΔII = molecule ΔII which has undergone deletion
Note: the numbering of the nucleotides and of the amino acids is that of Wood et al. (1).

EXAMPLE 1

Construction of plasmids carrying derivatives of the cDNA of the factor VIII which have undergone deletion in the region corresponding to domain B.

The starting plasmid is plasmid pTG1080 which carries the cDNA of factor VIII, nucleotdies −64 to 8230, cloned into the Sali site of pUC8 (this plasmid has been described in French Patent 86/08,258).

From this plasmid, 2 derivative were prepared, one (ΔI) comprising a deletion in domain B corresponding to amino acids 868 to 1562, the other (ΔII) corresponding to a deletion of amino acids 771 to 1666.

The construction ΔII hence abolishes the cleavage site at position 1649.

The two constructions are shown schematically in FIG. 2.

a) Plasmid pTG1080 was digested with the enzyme PstI to release a 2.7-kb fragment comprising 5' and corresponding to nucleotides −64 to 2641 of the cDNA of factor VIII.

This PstI fragment was cloned into the vector pTG1-POLY (a cloning vector derived from pML2, containing an origin of replication which is active in E. coli and the β-lactamase gene, into which a polylinker possessing 12 single restriction sites has been inserted). This vector is identical to the vector pTG14 described in Patent PCT-FR 85/00,096, with the exception of the polylinker which replaces the HindIII linker. In this construction, the BglII site of the polylinker is adjacent to the PstI site (nucleotide 2641) of the FVIII sequence.

The 3'-position of the FVIII coding sequence (nucleotides 4801 to 8230) is then introduced into this BglII site, in the form of a BamHI fragment also isolated from pTG1080.

The construction possessing the two FVIII segments in the correct orientation is referred to as pTG1501. The factor VIII cDNA sequence carried by this construction is referred to as FVIIIΔI. The PstI/BglII/-BamHI junction thereby formed preserves the FVIII reading frame.

b) From pTG1501, a KpnI-SphI fragment (corresponding to nucleotides 1811 to 6580) is recovered and introduced into the vector M13TG131 (20), and nucleotides 2367 to 5056 are deleted from it by the so-called "loop out mutaenesis" technique (17) with a synthetic oligonucleotide having the following sequence:

5'TCATTTCAACTGATATGGTGT-CAGTCTT3'

The vector which has undergone deletion is referred to as M13TG151O; the FVIII cDNA sequence which has undergone deletion is referred to as FVIII II. Sequencing analysis confirms that the sequence is correct.

EXAMPLE 2

Expression of the FVIIIΔI and ΔII sequences by recombinant vaccinia viruses.

In French Patent 86/08,258, plasmid pTG1016, which carries the cDNA sequence of factor VIII downstream from the promoter of the gene coding for the 7.5 K protein of the vaccinia virus, was described, and this expression block is inserted in the TK gene of vaccinia virus.

A derivative of plasmid pTG1016, pTG1030 (identical to the above except for the BglII-PstI deletion in the untranslated 5' region of the FVIII sequence) was used for integrating the constructions which have undergone deletions, FVIIIΔI and ΔII, in place of the native sequence, in the vector designed to permit integration in the vaccinia virus genome.

The BamHI-BglII fragment (corresponding to nucleotides 1864 to 6056) of the native sequence of pTG1030 is excised and replaced by the BamHI-BgII fragment of pTG1501 (FVIIIΔI) to give pTG1506, or by the BamHI-BgII fragment of M13TG1510 (FVIIIΔII) to give pTG1507).

The DNA blocks, comprising the TK gene of vaccinia interrupted by the FVIII cDNA placed under the vaccinia 7.5 K promoter, are integrated in the vaccinia virus genome, by homologous recombination, according to the classical technique (18).

The corresponding recombinant viruses are referred to as VV.TG.FVIII1506 FVIIIΔI) and VV.TG.FVIII1507 (FVIIΔII).

The recombinant viruses are used for infecting BHK21 cell lawns (2 × 10$^6$ cells) with 1 pfu/cell. After 1 hour's adsorption, the cultures are washed and replenished with fresh medium without serum, to which 1% BSA and 1 mM CaCl$_2$ has been added. Samples of medium are withdrawn after 24 and 48 hours and assayed for the quantity of factor VIII present, determined by immunoradiometric assay (FVIII:Ag), and for the procoagulant activity of the factor VIII (FVIII:C).

The FVIII or FVIIIΔ antigen is assayed by sandwiching it between the immunoglobulin G of the inhibitory serum of a hemophilic patient, the immunoglobulin being adsorbed on the wall of the test tube, and a radioactive anti-factor VIII monoclonal antibody specific for an epitope of the light chain, according to a method described by Lee et al. (21).

The measurement of the factor VIII activity (FVIII:C) is carried out in the classical manner by means of the activated partial thromboplastin time (APTT) (22).

The results are presented in the following table.

TABLE 1

Determination of the quantity of FVIII:Ag and of the FVIII:C procoagulant activity in the supernatant of BHK21 cultures infected with recombinant VV viruses (results expressed in mU/ml — threshold of detection = 1 mU/ml).

| Recombinant VV | 24 hours | | 48 hours | |
| --- | --- | --- | --- | --- |
| | FVIII:C | FVIII:Ag | FVIII:C | FVIII:Ag |
| VV.TG.1030 (FVIII) | 47.5 | 78.5 | 42.5 | 120.0 |
| VV.TG.1506-9 (FVIIIΔI) | 110.0 | 128.0 | 155.0 | 187.5 |
| VV.TG.1507-6 (FVIIIΔII) | 160.0 | 486.7 | 548.0 | 615.0 |

The results show that the two molecules which have undergone deletion are biologically active in a blood coagulation test, and that a larger quantity of protein is obtained with the FVIIIΔ constructions than with the intact FVIII (2-times increase with FVIIIΔI and 5-times increase with FVIIIΔII).

In addition, the FVIII:C activity does not fall between 24 and 48 hours, whereas it falls with the intact molecule. It is known that the latter has to be stabilized with the von Willebrand factor in order to retain its activity (French Patent 86/08,258).

EXAMPLE 3

Establishment of cell lines that express factor VIII or factor VIIIΔII.

1) Construction of plasmids

The coding sequences for factor VIII and for factor VIIIΔII were introduced into a vector, pTG384, designed for promoting its integration in the genome of mammalian cells in multicopy form. This vector has been described in French Patent 86/09,043. The important elements of this vector (see FIG. 3) are:

a) a murine mitochondrial DNA segment which promotes the integration of exogenous DNA sequences in the form of several copies in tandem (15).

b) an expression cassette comprising the enhancer (transcription activative) sequences of SV40 (72-bp repeat sequences), the major late promoter (MLP) of adenovirus 2, and the gene coding for the XGPRT xanthine:guanine phosphoribosyltransferase) selection marker. The vector is designed to enable a selected cDNA to be inserted on the 5' side of the XGPRT gene, so as to obtain a bicistronic transcription product. The vector also comprises, on the 3' side of the XGPRT, the intron of the small t antigen of SV40 and its polydenylation sequences.

c) the ColE1 origin of replication provides for the propagation of the vector E. coli.

The coding sequences for FVIII were inserted in the vector pTG384, in the single HindIII site (upstream from the XGPRT gene). The ends liberated by the HindIII digestion are made blunt by treatment with the Klenow fragment of DNA polymerase I.

The complete VBIII sequence is recovered from plasmid pTG1080 (see Example 1) in the form of an SmaI-HpaI fragment (the SmaI site is situated in the polylinker upstream from the initiator ATG, and the HpaI site is situated at nucleotide 7,434). The ligation of this fragment in the vector pTG384, opened with HindIII and treated with Klenow, gives plasmid pTG1020.

To perform the analogous construction with the factor VIII gene which has undergone deletion, the BamHI-BglI fragment (nucleotides 1864 and 6050 of FVIII) is exchanged, in pTG1020, with the FVIIIΔII fragment, BamHI-BglI of M13TG1510, according to the same principle as for the construction of pTG1507. The vector pTG304 which has inserted FVIIIΔII is referred to as pTG1507.

2) Transfection of CHO cells with plasmids pTG1020 and pTG1509.

Lawns of CHO cells were transfected with the DNA of plasmids pTG1020 (VFIII) or pTG1509 (FVIIIΔII) by the calcium phosphate precipitates method (19), with 5 or 10 μg of DNA per dish 8.5 cm in diameter. 48 hours after the transfection, the cells are trypsinized, diluted and inoculated in MEMα2000 selective medium supplemented with hypoxanthine (15 mg/l), thymidine (10 mg/l), xanthine (250 mg/l) aminopterin (0.2 mg/l), mycophenolic acid (25 mg/l) and 10% of dialyzed foetal calf serum.

After two weeks, the clones of cells resistant to the selective medium are removed and cultured in 1-ml and then 2-ml cups. When the cells reach 70% confluence, the medium is removed and the cell lawns are washed and replenished with fresh medium containing 5% of inactivated serum (to avoid a high background in the coagulation tests).

After 24 hours, the medium is harvested and analyzed for the presence (FVIII:Ag) and the activity (FVIII:C) of factor VIII.

Several clones were obtained. In the first analysis, most of the clones that express complete FVIII are seen to produce less material than the clones that express factor VIIIΔII.

Two clones were selected:

CHO-TG1020-22-12 which expresses complete FVIII and CHO-TG1509-18, which expresses FVIIIΔII.

The levels of FVIII expression and activity are presented in the following table:

TABLE 2

Determination of FVIII:Ag and FVIII:C (in mU) in the supernatant of CHO clones ($10^6$ cells), harvested after 24 hours.

|  | FVIII:Ag | FVIII:C |
|---|---|---|
| CHO-TG1020-22-12 | 63 | 60 |
| CHO-TG1509-18 | 504 | 500 |

A production of factor VIIIΔII 10-times greater than that of the complete factor VIII is observed, which confirms the results observed in the vaccinia model.

EXAMPLE 4

Activation by thrombin of the various native and recombinant factor VIII molecules.

Different factor VIII molecules were compared in a study of kinetics of activation by thrombin: native factor VIII derived from plasma and the recombinant factor VIII, complete and ΔII, expressed in the CHO clones.

The activation is measured in a classical coagulation test (APTT) after incubation in the presence of a catalytic amount of thrombin.

FIG. 4 shows that the recombinant FVIII and the plasma FVIII are activated in the same manner (by a factor of 20) and according to very similar kinetics. The FVIIIΔII is activated much more strongly (by a factor of 80 after 5 minutes' incubation with thrombin).

Although the factor VIIIΔII is much more strongly activated, it is not activated more rapidly than the other two molecules (in contrast to what has been observed by others (9) with the factor VIIIΔ constructions), thereby showing that factor VIIIΔII is not preactivated, which is important for the purpose of its therapeutic use.

The fact that FVIIIΔII is not preactivated is confirmed by the good correlation between the FVIII:Ag and FVIII:C levels, both in the vaccinia model and in CHO lines.

DEPOSITION OF STRAINS REPRESENTING THE INVENTION

The following strains were deposited with the Collection Nationale de Culture des Microorganismes, (National Collection of Microorganism Cultures), 25 Rue du Docteur Roux, Paris, on Jul. 24th 1987:

E. coli BJM83/pTG1020, under No. I-679
E. coli 5K/pTG1507, under No. I-680
E. coli BJ1509/pTG1509, under No. I-681

REFERENCES

1) Wood, W. I. et al. Nature 312, 330 (1984).
2) Toole, J. J. et al. Nature 312, 342 (1984).
3) Truett, M. A. et al. DNA 4, 333 (1985).
4) Vehar, G. A. et al. Nature 312, 337 (1984).
5) Gitschier, J. et al. Nature 312, 326 (1984).
6) Fulcher, C. A. et al. Blood 61, 807 (1983).
7) Eaton, D. L. et al. Biochemistry 25, 505 (1986).
8) Toole, J. J. et al. Proc. Natl. Acad. Sci. USA 83, 5939 (1986).
9) Eaton, D. L. et al. Biochemistry 25, 8343 (1986).
10) Burke, R. L. et al. Biol. Chem. 261, 12574 (1986).
11) Pavirani, A. et al. In press.
12) Pavirani, A. et al. Bio/Technology (1987).
13) Mulligen, R. C. and Berg, P. Proc. Natl. Acad. Sci. USA 78, 2072–2076 1981).
14) De La Salle, H. and Elkaim, R. French Patent No. 86.09043.
15) Lutfalla et al. Somatic cell and Mol. Genet. 11, 223–238.
16) Brinkhous, K. M. et al. Proc. Natl. Acad. Sci. USA 82, 8752–8756 (1985).
17) Zoller, M. J. and Smith, M. Methods Enzymol. 100B, 408–500 (1983).
18) Kieny, M. P. et al Nature 312, 163–166 (1984).
19) Graham, F. L. and van der Eb, A. J. Virology 52, 456–467 (1973).
20) Kieny, M. P., Lathe, R. and Lecocq, J. P. Gene 26, 91–99 (1983).
21) Lee, M. L., Maghalang, E. A. and Kingdon, M. J. Thromb. Res. 30, 511–519 (1983).
22) Girma, J. P., Lavergne, J. M., Meyer, D. and Larrien, M. J. Br. J. Haematol. 47, 269–282 (1981).

We claim:

1. A human factor VIII analog consisting essentially of the amino acid sequence alanine-1 through aspartate-770 followed by threonine-1667 through tyrosine-2332, wherein aspartate-770 is covalently bonded by a peptide bond to threonine-1667.

2. A glycosylated human factor VIII analog consisting essentially of the amino acid sequence alanine-1 through aspartate-770 followed by threonine-1667 through tyrosine-2332, wherein aspartate-770 is covalently bonded by a peptide bond to threonine-1667.

3. A pharmaceutical composition comprising, by way of active principle, a human factor VIII analog consisting essentially of the amino acid sequence alanine-1 through aspartate-770 followed by threonine-1667 through tyrosine-2332, wherein aspartate-770 is covalently bonded by a peptide bond to threonine-1667.

4. A pharmaceutical composition comprising, by way of active principle, a human factor VIII analog consisting essentially of the amino acid sequence alanine-1 through aspartate-770 followed by threonine-1667 through tyrosine-2332, wherein aspartate-770 is covalently bonded by a peptide bond to threonine-1667, said pharmaceutical composition further including the von Willebrand factor.

5. The pharmaceutical composition as claimed in claim 3 in sterile injectable form.

6. The pharmaceutical composition as claimed in claim 4 in sterile injectable form.

* * * * *